United States Patent [19]

Carim

[11] 4,406,827
[45] Sep. 27, 1983

[54] COHESIVE NONSTICKY ELECTRICALLY CONDUCTIVE GEL COMPOSITION

[75] Inventor: Hatim M. Carim, St. Paul, Minn.

[73] Assignee: Minnesota Mining and Manufacturing Company, St. Paul, Minn.

[21] Appl. No.: 72,230

[22] Filed: Sep. 4, 1979

[51] Int. Cl.³ .............................................. H01B 1/06
[52] U.S. Cl. .................................. 252/518; 252/519; 128/639
[58] Field of Search ............... 252/518, 519, 316, 500, 252/511; 128/639, 640, 641, 803, 798, 419 R; 106/205, 208

[56] References Cited

U.S. PATENT DOCUMENTS

| | | | |
|---|---|---|---|
| 3,072,509 | 1/1963 | Barnhart et al. | 149/55 |
| 3,301,723 | 1/1967 | Chrisp | 252/316 |
| 3,989,050 | 11/1976 | Buchalter | 128/419 R |
| 4,125,110 | 11/1978 | Hymes | 128/641 |

*Primary Examiner*—Josephine Barr
*Attorney, Agent, or Firm*—Cruzan Alexander; Donald M. Sell; Jennie G. Boeder

[57] ABSTRACT

A cohesive nonsticky electrically conductive gel is disclosed, for facilitating low resistance contact between a metal electrode and a biological body. The gel comprises an aqueous solution of up to saturated concentrations of ionized salts as the conducting agent, a natural gum capable of crosslinking, and a crosslinking material which provides the electrically conductive gel with sufficient internal strength to remain cohesive without reinforcement. The gel has good electrical characteristics and improved physical properties which prevent the gel from leaving a messy residue on the skin of the patient or on the electrode.

18 Claims, No Drawings

COHESIVE NONSTICKY ELECTRICALLY CONDUCTIVE GEL COMPOSITION

BACKGROUND OF THE INVENTION

The present invention relates generally to electrically conductive gels which are used to transmit an electrical signal between the human skin and an electrode attached to an electrical recording or stimulating device.

Frequently in the practice of medicine it is desirable to make electrical contact with the body. Such contact may be for the purpose of measuring electrical signals, as in the making of electrocardiograms or electroencephalograms, or applying electrical impulses to the body during electrotherapy.

The skin is a difficult structure with which to make reliable, low resistance, electrical contact. Accordingly, it has become customary in the art to utilize a conductive medium between the electrode and the skin to enhance conductivity. This medium normally takes the form of a conductive paste or gel which makes intimate contact with the skin, by conforming to the contours of the skin, and fills the gaps between the skin and the electrode, thus providing a more reliable path for the electrical current than is afforded by dry surface contact between electrode and skin. These gels or pastes are normally made of a thickened aqueous mixture containing a conductive salt, such as sodium chloride. Conventional thickening agents typically include polymers, such as polyvinylalcohol (commonly referred to as PVA), polyethylene glycol or polypropylene glycol; glycerol and glycerol derivatives, such as glycerol monostearate; and a number of naturally occurring gummy materials, such as gum tragacanth, sodium alginate, locust bean gum and guar gum. A number of synthetic gummy materials and thickeners have also been used, including carboxymethyl cellulose, and proprietary materials such as Ganatrez materials sold by General Aniline and Film Corporation and Carbopols sold by the B. F. Goodrich Co.

Examples of the gels or pastes of the prior art can be found in U.S. Pat. Nos. 4,016,869; 3,998,215; 3,989,050; 3,658,726; and 3,265,638. These gels and creams are comprised of a thickened aqueous mixture and a salt or polarizing substance and do a reasonably effective job of making electrical contact with the skin. In particular, they make possible a contact which is largely free of voids and areas of poor or intermittent contact, which, when present, result in the generation of spurious electrical signals. Such spurious signals interfere with the collection of desired electrical data. However, all of these gels have one major disadvantage. They are sticky, messy materials which are unpleasant to use and are hard to remove from surfaces they have contacted. This problem has been addressed in the art by reinforcing the gelatinous or creamy conductive materials with porous or fibrous substances, which help to contain the gel or cream in a cohesive matrix, see U.S. Pat. No. 3,998,215. These structures, often referred to as gel pads, function well in regard to making good electrical contact with skin. However, the addition of nonconductive structural members within the conductive gel inevitably alters the resistance of a gel pad relative to that of the pure gel.

Germam Offenlegangschrift No. 27 27 396 discloses a viscoelastic conductive gel comprising a high molecular weight polysaccharide and a polyol, which is said to leave behind no residue on the skin. The gels disclosed therein are not crosslinked, have a low water content, are capable of carrying little salt and require the use of high molecular weight (at least about $10^6$) polysaccharides in order to provide the necessary cohesivity to be removed without leaving a residue. The low water content of these gels and their consequent inability to tolerate high salt levels limits their conductivity and sensitivity to electrical stimuli.

The gels of the present invention are an improvement over prior art gels. They maintain themselves as a cohesive mass without the need for mechanical reinforcement. They do not leave a residue on the skin or the electrode. Furthermore, they are capable of tolerating high concentrations of salt without breakdown of the gel. The gels of the present invention are less expensive to produce than the gels of the prior art since they can contain relatively less thickener and more water while still maintaining sufficient cohesive strength.

SUMMARY OF THE INVENTION

The present invention provides an electrically conductive gel for use in establishing a low resistance contact between an electrode and a biological body, comprising an aqueous solution of a natural gum capable of crosslinking and a crosslinking agent. The gum and crosslinking agent are present in quantities sufficient to impart a gel-like body to the material and to provide the electrically conductive gel with sufficient internal strength to remain cohesive without reinforcement. The gel material is capable of containing up to saturated concentrations of ionized salt without breakdown of the crosslinked gel. The gel material is non-sticky in character.

The gel of the instant invention provides a conductive, conformable interface between the skin and the electrodes placed thereon thus preventing electrical noise interference, and additionally is easy to apply, removable without leaving a residue, and has sufficient strength of itself to perform well without reinforcement.

Although approximately 70% water, the gel stays together in a cohesive mass rather than spreading and sticking to surfaces with which it comes in contact. In this connection "cohesive" should be interpreted to mean that the gel has more adhesion to itself than to the surface of the skin and, thus, is capable of maintaining internal integrity and lifting from the skin without leaving a residue.

The instant invention provides a gel which conducts small electrical signals faithfully and which produces no artifacts of its own to degrade the signal.

The gel is physically stable over a wide temperature range, i.e., its flow and cohesive properties are essentially the same over the range of 0° to 60° C.

The gel of the present invention is resistant to drying out.

The gel can be used on the skin routinely with a minimum of irritation to the skin.

In addition, the gels of the present invention are stable in the presence of any practical salt concentration. Thus, even in the presence of saturated sodium chloride the crosslinked gels of the present invention will not break down. This feature is in contrast to crosslinked gels based on polyvinyl chloride which will break down in the presence of salt concentrations much lower than saturation, i.e., 10 percent NaCl higher than about 5 percent. Furthermore, the gel is not adversely affected by exudates from the skin, such as perspiration.

The gels of the present invention can be used as a conductive medium on a patient's skin before emplacing an electrode or in a pre-assembled electrode. An example of the former use is in emergency situations where a patient is suffering from cardiac distress. Dabs of gel are dispensed onto the patient's skin in a standard pattern over the heart area. Electrodes are attached to these portions and are connected to an electrocardiograph, the read-out of which, commonly called an E.C.G., provides an indication of the patient's heart condition. For long-term monitoring of heart-function it is preferred to use the gel in a pre-assembled electrode, referred to as a "monitoring electrode". Such an electrode comprises an electrode plate having on one surface thereof means for electrical connection to an electromedical apparatus and on the opposite, body contacting surface thereof, the electrically conductive gel material of the present invention. Descriptions of pre-assembled electrodes are contained in assignee's copending patent applications, U.S. Ser. Nos. 940,735 and 940,734, both filed on Sept. 8, 1978 and incorporated herein by reference. In both uses the gel is applied and electrical contact achieved with light finger pressure. After use the gel may simply be lifted off the skin in a cohesive mass without leaving a sticky residue.

Although the gel of this invention is particularly useful as a conductive medium between the skin and a biopotential monitoring electrode suitable for detecting the very small electrical signals, such as are characteristic of E.C.G. measurements, it is not limited to this use. For example, the gel can be used as the conductive medium between defibrillation electrodes and the skin of a patient whose heart is in fibrillation. In such a case high voltages are required in order to electrically shock the heart into beating. A major advantage of the new gel in this use is that it does not smear or flow rapidly over a surface, thus avoiding the creation of a potentially dangerous conductive path; possibly over a patient's chest. An added advantage of the gel of the present invention is the greatly reduced chore of cleanup. Since the electrodes used in defibrillation are large, a substantial proportion of the patient's chest can become covered with conductive medium. The cohesive, non-sticky gel of the present invention greatly eases cleanup of the patient.

Another use of the present invention is as an electroconductive medium for an electrosurgical ground plate. Still another use of the present gel is as the conductive medium between the skin and electrodes of the type used for transcutaneous nerve stimulation or for pain relief. These electrodes are often in the form of metal plates or foils.

It should be pointed out that while the gel can be used advantageously with electrosurgical grounding plates or with transcutaneous nerve stimultion electrodes, as described above, the preferred embodiment of the gel has limitations in conditions where it is under pressure. The compositions have the ability to cold flow; that is, when placed in a vessel the gum will eventually acquire the shape of the inside of the vessel. By this means, the ability of the gel to conform accurately to the contours of, for example, the skin and the undersurface of an electrode, is assured. In practice, a momentary light finger pressure is all that is required to emplace an electrode properly on the skin. However, due to its ability to cold flow, the gel will spread slowly under pressure, and if squeezed for a long time, such as when placed under a supine patient undergoing lengthy surgery, it could be squeezed out beyond the immediate area of the electrode plate. Under these conditions, a restraining means can be used to keep the gel in place. A porous fibrous material, such as a pouch of inert porous woven or nonwoven fabric placed around the gel can be used as a restraining means. An open-cell foam, such as one of the polyurethane foams, impregnated with the gel may also be used.

DETAILED DESCRIPTION

The present invention provides an electrolyte gel based on a crosslinked natural gum as the thickening agent. The preferred gums are guar gum and locust bean gum. Structurally, the useful natural gums are high polymeric saccharides comprised of hexose, pentose or uronic acid groups linked together.

One feature of the natural gums is their ready availability and low cost. A feature of guar gum is that it can be obtained in a rather pure state without extensive processing. Guar gum in its natural state is relatively pure, having very few impurities such as sulphur (sometimes found in agar) or extraneous ions (as found in many of the less pure gums).

A useful practical feature of guar gum gels is that they can be produced at room temperature or at only slightly raised temperature due to the fact that guar gum powder mixes well with room temperature water unlike synthetic gels such as polyvinyl alcohol which requires heating and more complicated production techniques. In addition, the natural pH of guar gum gels of this invention is approximately 7–8.5, which is an excellent pH range for a composition to be used against the skin since it is close to the physiological pH. Gels of the prior art have been neutralized or buffered in order to achieve an acceptable pH.

Natural gums are polysaccharides obtained from natural substances. For example, guar gum is a polysaccharide obtained from the seeds of the guar plant. The structure of guar gum, as illustrated below, is that of a chain mannose sacharide polymer with repeating single-unit galactose branches, referred to as galactomannan.

Structure of guar gum

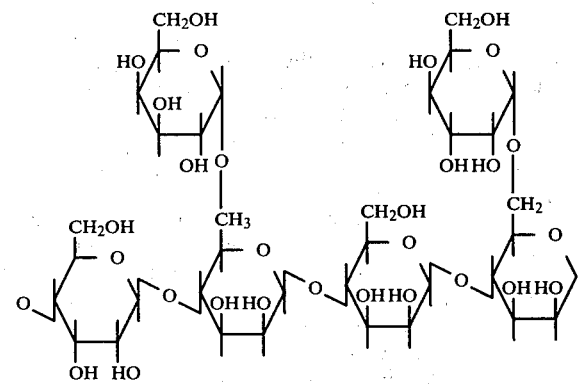

Guar gum is available in anionic, cationic and nonionic forms. The nonionic type has been found most suitable for use with Ag/AgCl electrodes and is preferred for use with sensitive biomonitoring electrodes. Applicant has surprisingly found that gels made from a hydroxy-propylated nonionic guar gum, sold by the Stein Hall Co. under the trademark JAGUAR® HP-11, are stable to concentrations of chloride ion greater than 10 percent by weight. Thus, this guar gum gel can be successfully utilized where the transmission of high currents is desired (i.e., high salt concentrations are required) without breakdown of the gel's cohesive structure. However, in applications where the electrodes are to contact the skin for periods longer than an hour, lower concentrations, 0.1–5 percent by weight, of chloride ion are preferred. The lower concentrations of chloride are also preferred for electrodes which have been gelled and stored a long time prior to use in order to avoid corrosion effects on other parts of the electrode.

Both anionic and cationic guars are also useful as conductive gels. Anionic guar, sold by the Stein Hall Co. under the trademark JAGUAR® CMHP, and cationic guar, sold by the Stein Hall Co. under the trademark JAGUAR® C-13, have been successfully tested. Additionally, even a food-grade guar has been used successfully. Gels made from these gums are of different viscosities and achieve peak viscosity at different times than do gels made from nonionic guar gum.

Mixtures of crosslinkable natural gums with other thickeners are also within the scope of the present invention. For example, the addition of polyvinyl alcohol (PVA) to guar gum increases the cohesive strength of the final gel, and decreases its cold flow. This formulation is not particularly advantageous for biomonitoring electrodes, but can be valuable in electrodes where the gel is under high compressive loads, such as in electrosurgery or in transcutaneous nerve stimulation. Other thickeners which can be mixed with the crosslinkable natural gums include hydroxyethyl cellulose, and hydroxypropyl methyl cellulose. Examples of other natural gums which can be mixed with the crosslinkable natural gums of the present invention include gum Arabic, sodium alginate and gum tragacanth.

The gels of the present invention have increased internal cohesiveness and are able to be easily removed from surfaces with which they come in contact due to their crosslinked nature. The preferred crosslinking agent is borate ion, supplied by potassium tetraborate or sodium tetraborate. Borate ion reacts effectively with the preferred gums, guar gum and locust bean gum, to form stable gels. In addition compositions crosslinked with borate are acceptable for contact with human skin.

The exact nature of the crosslinking of guar gum with borate ion is not well understood. A degree of ester formation between the borate anions and the hydroxyl groups of the gums is possible. The formation of coordinate bonds would also account for the observed crosslinking effect. It is noted that polysaccharides with cis-hydroxyl groups on adjacent chains, such as guar gum and locust bean gum, are those most usefully crosslinked by borate ions for purposes of this invention. That is, gels made with polysaccharides having cis-hydroxyl groups exhibit the greatest degree of crosslinking (e.g., the stiffest gel is produced) for given concentrations of gum and borate. It is possible that borate ion reacts with polysaccharides containing cis-hydroxyl groups to form bridges between adjacent cis-polyhydroxy moieties on different polymeric molecules.

Other crosslinking agents useful in the gels of the present invention include salts, such as ferric chloride, calcium chloride and the acetates of the multivalent cations of lead, chromium or nickel. Those skilled in the art will recognize that by careful manipulation of reaction conditions, e.g., temperature, pH, agitation, time of reaction, etc., a degree of crosslinking can be achieved in the gel without the use of these crosslinking agents. Such crosslinking can be detected by viscosity changes or by gel formations. However, the difficulty in preparing a stable medically-acceptable gel makes the above means of crosslinking less desirable than the borate-guar system.

The preferred embodiment of the present invention includes within the crosslinked gum, any salt suitable to act as a conductor for the passage of electric current from an electrode to the body of a patient. However, crosslinked gums containing no salt are also contemplated since the gels of the present invention are aqueous in major portions and can conduct a current when subjected to high voltages. The preferred salts are chlorides, particularly those of sodium or potassium, since these are the most compatible with the normal electrolytes within the body. The chlorides are particularly preferred for use with the very sensitive Ag/AgCl (Silver/Silver Chloride) electrodes, as they take part in the cell reaction and contribute to the proper functioning of the electrode. As previously mentioned the Ag/AgCl electrodes are particularly well suited for measuring minute electrical bio-events.

The electrolyte concentration is important as it affects both current carrying capacity and skin irritation. For monitoring purposes, where electrodes may be worn for days at a time, it is desirable to keep the salt concentration below about 3%. Higher salt concentrations become irritating to the skin when in contact for prolonged periods and may cause serious lesions in the most severe cases.

For short-term use as in cardiac stress testing, electrotherapy or electrosurgery, where the total contact time may be less than one hour, much higher salt concentrations can be used. The low electrical resistance necessary for the above-mentioned uses can only be exhibited by gels with high concentrations of electrolyte. A surprising feature of the crosslinked gels of the present invention are their stability even in the presence of saturated sodium chloride, approximately 25 percent by weight. Thus, the present invention provides a gel which is stable in the presence of essentially any salt concentration desired.

Electrode storage time is another factor in the determination of electrolyte type and concentration. Lower salt concentrations are preferred when electrodes are to be stored a long time between manufacture and use. Salt solutions of sodium chloride and potassium chloride are corrosive to ferrous metals, with the result that gels high in concentrations of these salts may corrode the electrodes when in contact with the electrodes over a sufficiently long period of time. Where storage periods are long and higher salt concentrations are desired, salts less corrosive than sodium chloride or potassium chloride, such as sodium citrate, should be used.

The choice of electrolyte is also affected by electrode composition. Where electrodes made of aluminum, stainless steel or German silver (a silver-white alloy of copper, zinc and nickel) are employed for biomonitoring purposes spurious signals or electrical noise are commonly experienced. Such signals are thought to be generated by chemical reactions taking place between the electrode and corrosive conductive salts, such as sodium chloride. Potassium citrate can be substituted for more corrosive salts, in order to reduce electrical noise.

Another aspect of the present invention may include the presence of humectants, plasticizers, and wetting agents in the crosslinked gel. Humectants increase the ability of the gel to resist drying out when exposed to the atmosphere or to conditions of low humidity. Plasticizers add smoothness and increased pliability to the gel. Wetting agents permit the gel powder to disperse in water in a homogeneous and lump-free manner. 1,3-Butylene glycol, tetrahydrofurfuryl alcohol and dipropylene glycol are known plasticizers and humectants. Diethylene glycol and glycerol have been commonly utilized as humectants. However, glycerol competes with guar gum for borate, and can interfere with proper gel formation by inhibiting crosslinking if present in sufficient quantity. Propylene glycol can function in the gels of the present invention as a humectant, a plasticizer and a wetting agent for guar gum powder during manufacture.

The gels of the present invention may also contain preservatives to prevent bacterial growth during storage and use. The parabens, e.g., methyl and propyl-p-hydroxy-benzoates, are well-accepted preservatives for use in medicinal preparations.

Preferred components and concentrations for the gels of the present invention follow. All percentages are given in percents by weight.

| Component | Percent by Weight |
|---|---|
| Guar gum (sold by the Stein Hall Co. under the trademark JAGUAR ® HP-11) | 1 to 5% |
| NaCL | 0.8 to 25% |
| Potassium Tetraborate ($K_2B_4O_7.5H_2O$) | 0.05 to 3.0% |
| Propylene glycol | 5 to 50% |
| Propyl-p-hydroxy benzoate (propylparaben) | 0.01 to 0.05% |
| Methyl-p-hydroxybenzoate (methylparaben) | 0.01 to 0.9% |
| Water | to 100% |

In general altering the proportions of the components has the following effects:

Raising the amount of guar gum increases the viscosity of the gel, and conversely lowering the amount of guar gum decreases the viscosity of the gel.

Raising the chloride ion concentration increases the electrical conductivity of the gel and decreases the gel-skin impedance, and conversely lowering the chloride ion concentration decreases the electrical conductivity of the gel and increases gel-skin impedance.

Raising the borate ion concentration increases the degree of crosslinking and the stiffness of the gel, and conversely lowering the borate ion concentration decreases the degree of crosslinking and thus the stiffness of the gel.

Raising the amount of propylene glycol, a humectant, increases the ability of the gel to resist drying out.

Raising the concentration of the parabens increases the bacteriostatic ability of the gel.

An especially preferred composition for use in the practice of the present invention, particularly with a biomonitoring electrode, is the following:

| Component | Percent by weight |
|---|---|
| Guar gum (HP-11, Stein Hall & Co.) | 2.0 |
| NaCl | 2.4 |
| Propylene glycol | 15.0 |

-continued

| Component | Percent by weight |
|---|---|
| Methyl-p-hydroxy benzoate | 0.1 |
| Propyl-p-hydroxy benzoate | 0.02 |
| Potassium Tetraborate | 0.57 |
| Water | to 100 |

This composition has excellent electrical properties in addition to a useful combination of physical properties. The gel makes good contact with both skin and electrode, is stable with regard to moisture loss (a major factor affecting shelf-life and useful life on patient), and possesses excellent cohesive strength.

The following examples further illustrate the present invention. In these Examples, all parts and percents are by weight, unless otherwise indicated.

EXAMPLE 1

Approximately 300 ml of distilled water is heated in a 600 ml beaker to a temperature of 60°–75° C. and 9.9 gm of sodium chloride is added to the heated water with stirring until dissolved. In a separate vessel, 0.16 gm of propyl-p-hydroxy benzoate and 0.8 gm of methyl-p-hydroxy benzoate are mixed well with 80.0 gm of propylene glycol until dissolved. To this mixture 6.4 gm of guar gum powder (commercially available as JAGUAR ® HP-11 from the Stein Hall Co.) is added slowly with constant stirring until homogeneously dispersed.

The dispersion of guar gum in paraben/propylene glycol solution is added slowly to the aqueous sodium chloride solution with vigorous stirring, e.g., with a high shear mixer (Homo-mixer commercially available from Gifford Wood, Inc., Hudson, N.Y.). Vigorous mixing is continued and the temperature is maintained at about 60°–75° C. until the mixture is smooth and the guar gum is completely dissolved (about 10–20 minutes). The resultant mixture is a homogenous, viscous solution. The heat source is removed and vigorous mixing is continued while 20 ml of a 10% w/v solution of potassium tetraborate is slowly added. The stirring is discontinued and the mixture is allowed to cool to room temperature.

EXAMPLES 2–7

Following the procedure of Example 1 gels were prepared having the following compositions:

| Example Number | Gum | Amount Gum (% by wt.) | Amount potassium tetraborate (% by wt.) | Amount NaCl/KCL* (% by wt.) |
|---|---|---|---|---|
| 2 | Guar (JAGUAR ® CMHP) | 1.6 | 0.5 | 2.4 |
| 3 | Guar (JAGUAR ® C-13) | 1.6 | 0.5 | 2.4 |
| 4 | Locust Bean | 1.6 | 0.375 | 2.4 |
| 5 | GUAR (JAGUAR ® HP-11) | 1.6 | 0.583 | 2.4 |
| 6 | GUAR (JAGUAR ® C-13) | 1.6 | 0.5 | 30.0* |
| 7 | GUAR (JAGUAR HP-11) | 1.6 | 0.5 | 30.0* |

Examples 6 and 7 illustrate that a gel can be made according to the present invention which can accomodate high salt concentrations.

EXAMPLE 8

Approximately 300 ml of distilled water is heated in a 600 ml beaker to a temperature of 60°-75° C. 9.9 gm of sodium chloride, 0.16 gm of propyl-p-hydroxy benzoate and 6.4 gm of guar gum powder (commercially available as JAGUAR ® A2S from the Stein Hall Co.) are added to the water and the mixture is stirred vigorously, e.g., with a Homo-mixer, until a homogeneous mixture is obtained (15-20 minutes). The heat source is removed and, using moderate stirring (e.g., with a propeller-type stirrer), a 10% w/v solution of potassium tetraborate, and propylene glycol are slowly added in alternate aliquots over a period of about 5-10 minutes as follows:
1. 2-5 ml 10% w/v solution of potassium tetraborate (until gelation starts).
2. 10 gms propylene glycol.

Thereafter 2 ml aliquots of the 10% potassium tetraborate solution are alternated with 10 gm aliquots of propylene glycol until a total of 20 ml of the potassium tetraborate solution and 80 gms of propylene glycol have been added. Upon cooling, a gel of this invention is obtained.

EXAMPLE 9

Following the procedure of Example 8 a gel was prepared having the following composition:

| Example Number | Gum | Amount Gum (% by wt.) | Amount potassium tetraborate (% by wt.) | Amount NaCl (% by wt.) |
|---|---|---|---|---|
| 9 | GUAR (JAGUAR ® A-40-(F)) | 1.6 | 0.25 | 2.4 |

The following table (Table I) is a list of the physical properties of the gels of Examples (1-9).

TABLE I

| Example Number | Gum | Amount Gum (% by wt.) | Amount potassium tetraborate | pH of crosslinked gel | Electrical Resistivity ohm-cm at 10 KHz | NaCl/KCL* (% by wt.) | Viscosity (Poise) at Shear Rate | |
|---|---|---|---|---|---|---|---|---|
| | | | | | | | 0.025/sec. | 0.1/sec. |
| 1 | Guar (HP-11) | 1.6 | 0.50 | 7.66 | 42.8 | 2.4 | $11.8 \times 10^3$ | $5.2 \times 10^3$ |
| 2 | Guar (CMHP) | 1.6 | 0.50 | 7.70 | 44.0 | 2.4 | $12.0 \times 10^3$ | $5.5 \times 10^3$ |
| 3 | Guar (C-13) | 1.6 | 0.50 | 7.66 | 43.7 | 2.4 | $20.0 \times 10^3$ | $9.6 \times 10^3$ |
| 4 | Locust Bean | 1.6 | 0.375 | 7.65 | 42.8 | 2.4 | $20.0 \times 10^3$ | — |
| 5 | Guar (HP-11) | 1.6 | 0.583 | 7.6 | 18.4 | 6.4 | $9.2 \times 10^3$ | — |
| 6 | Guar (C-13) | 1.6 | 0.5 | 7.6 | 6.8 | 30.0* | — | — |
| 7 | Guar (HP-11) | 1.6 | 0.5 | 7.8 | 5.4 | 30.0* | — | — |
| 8 | Guar (A2S) | 1.6 | 0.50 | 7.35 | 41.5 | 2.4 | $2.0 \times 10^3$ | $1.7 \times 10^3$ |
| 9 | Guar (A40F) | 1.6 | 0.25 | 7.60 | 43.8 | 2.4 | $11.7 \times 10^3$ | $8.3 \times 10^3$ |

The viscosities of the gels of Examples 6 and 7 were not measured since these gels were prepared to show high salt concentration capability.

Electrical resistivity was measured using a plastic cell of approximately 3 c.c. volume. The cell consisted of two circular platinized platinum electrodes approximately 0.7 cm in diameter, which faced each other and were approximately 0.8 cm. apart. The cell constant (K cell) was calculated according to known experimental technique (see American Society of Testing Materials Standards, report Number D202-77, part 39, section 48, pp. 73, 1978 Annual) and found to be equal to 1.39 at 10 KHz (sinusoidal signal).

Resistivity measurements were taken at 10 KHz (sinusoidal signal) using a Hewlett Packard Model 4800 A vector impedance meter. A 10 KHz frequency was chosen to minimize electrode polarization effects. The cell was filled with the appropriate gel and its measured resistance (Rm) was obtained. Resistivity ($\rho$) is given in ohm-cm by the equation $$(\rho) = Rm \times Kcell = Rm \times 1.39 \text{ at 10 KHz}$$

All viscosity measurements were made using a mechanical spectrometer (Model RMS-7200 made by Rheometrics, Inc.) and according to the instrument instruction manual, using a 72 mm diameter cone and plate, a 0.04 radian angle and a 0.05 mm gap. All measurements were made at room temperature (18 25° C.).

EXAMPLE 10

A 1.6% by weight solution of JAGUAR ® HP-11 in distilled water was prepared. To a 40 c.c. sample of the guar gum solution approximately 1 c.c. of a 10% by weight solution of $FeCl_3$ in water was added with stirring. To this a concentrated solution of potassium hydroxide was added dropwise and the pH of the mixture was monitored. When the pH rose to an alkaline pH of about 11.2, from a starting pH of about 2.25, a crosslinked, cohesive, non-sticky gel was obtained.

EXAMPLE 11

A 1.6% by weight solution of JAGUAR ® CMHP in distilled water was prepared. To a 20 gm sample of the guar gum solution, 15 drops of a 10% by weight solution of chromium acetate was added with stirring. A concentrated solution of potassium hydroxide was then added dropwise to the mixture with stirring and the pH was monitored. At an alkaline pH of above about 9, an excellent crosslinked gel of the present invention was obtained. Subsequently 20 drops of a saturated solution of potassium chloride was mixed with the gel. The gel remained crosslinked, cohesive and non-sticky.

I claim:
1. An electrically conductive gel for use in establishing a low resistance contact between an electrode and a biological body, comprising an aqueous solution of crosslinked natural gum, said crosslinked natural gum being present in said aqueous solution in sufficient quantity to impart a gel-like body to the material and to provide the electrically conductive gel with sufficient internal strength to remain cohesive without reinforcement, said aqueous solution comprising ionized salts in a concentration of 0.8 to 25 percent by weight, and water in a concentration of from about 16 to 93 percent by weight, and said gel being nonsticky in character.

2. The electrically conductive gel of claim 1, wherein said natural gum is a polysaccharide having cis-hydroxyl groups.

3. The electrically conductive gel of claim 1 wherein said natural gum is selected from the group consisting of guar gum and locust bean gum.

4. The electrically conductive gel of claim 2, wherein said gel further comprises a thickening substance selected from the group consisting of sodium alginate, gum tragacanth, gum Arabic, hydroxyethyl cellulose, hydroxypropyl methyl cellulose, and polyvinyl alcohol.

5. The electrically conductive gel of claim 1 wherein said ionizable salt is selected from the group consisting of sodium chloride, potassium chloride, potassium citrate and calcium chloride.

6. The electrically conductive gel of claim 1, wherein said crosslinked natural gum is crosslinked with a crosslinking agent selected from the group consisting of borate ion, lead acetate, chromium acetate, nickel acetate, calcium chloride, and ferric chloride.

7. The electrically conductive gel of claim 1, wherein:
 (a) said ionized salt is sodium chloride;
 (b) said natural gum is guar gum, present in an amount of between about 1 and 5 percent by weight of said gel; and
 (c) said crosslinked natural gum is crosslinked with a crosslinking agent of potassium tetraborate present in an amount of between 0.05 and 3.0 percent by weight of said gel.

8. The electrically conductive gel of claim 1 wherein said gel further comprises a plasticizer.

9. The electrically conductive gel of claim 1 wherein said gel further comprises a humectant.

10. The electrically conductive gel of claim 1 wherein said gel further comprises a wetting agent for said thickening agent.

11. The electrically conductive gel of claim 1 wherein said gel further comprises a bactericide.

12. The electrically conductive gel of claim 11, wherein said bactericide is a paraben.

13. The electrically conductive gel of claim 7, wherein said gel further comprises:
 (a) propylene glycol in an amount of between about 5 and 50 percent by weight of said gel;
 (b) propyl-p-hydroxy benzoate in an amount of between about 0.01 and 0.05 percent by weight of said gel; and
 (c) methyl-p-hydroxybenzoate in an amount of between about 0.01 to 0.9 percent by weight of said gel.

14. An electrically conductive gel for use in establishing a low resistance contact between a metal electrode and a biological body, comprising:
 (a) about 2.4 percent by weight sodium chloride;
 (b) about 2.0 percent by weight guar gum;
 (c) about 0.57 percent by weight potassium tetraborate;
 (d) about 15.0 percent by weight propylene glycol;
 (e) about 0.1 percent by weight methyl-p-hydroxy benzoate;
 (f) about 0.02 percent by weight propyl-p-hydroxy benzoate; and
 (g) about 79.91 percent by weight water.

15. In a pre-assembled biomedical electrode comprising an electrode element, means attached to said electrode element for connecting a lead wire, and a conductive material on the body contacting surface of said electrode element for enhancing electrical connection with the skin, the improvement wherein said conductive material comprises the electrically conductive gel of claim 1.

16. In a pre-assembled biomedical electrode comprising an electrode element, means attached to said electrode element for connecting a lead wire, and a conductive material on the body contacting surface of said electrode element for enhancing electrical connection with the skin, the improvement wherein said conductive material comprises the electrically conductive gel of claim 6.

17. A method of making low resistance electrical contact between a metal electrode and a biological body comprising applying between the electrode and the body the electrically conductive gel of claim 1.

18. An electrically conductive pad conformable to the surface of the human body and adapted to facilitate the transfer of electrical signals between the body and an electrode, comprising a porous, fibrous carrier having the electrically conductive gel of claim 1 carried thereby, said gel impregnating and surfacing both sides of said carrier.

* * * * *

UNITED STATES PATENT AND TRADEMARK OFFICE
CERTIFICATE OF CORRECTION

PATENT NO. : 4,406,827

DATED : September 27, 1983

INVENTOR(S) : Hatim M. Carim

It is certified that error appears in the above-identified patent and that said Letters Patent is hereby corrected as shown below:

Col. 10, line 18, "18 25°C" should read -- ~25°C --.

Signed and Sealed this

Thirtieth Day of September 1986

[SEAL]

Attest:

DONALD J. QUIGG

*Attesting Officer*     *Commissioner of Patents and Trademarks*